(12) United States Patent
Glenn et al.

(10) Patent No.: US 12,090,141 B2
(45) Date of Patent: Sep. 17, 2024

(54) USE OF CLEMIZOLE COMPOUNDS FOR TREATMENT OF INFLAMMATORY CONDITIONS

(71) Applicant: Eiger Group International, Inc., Palo Alto, CA (US)

(72) Inventors: Jeffrey S. Glenn, Palo Alto, CA (US); Edward A. Pham, Shaker Heights, OH (US)

(73) Assignee: Eiger Group International, Inc., Palo Alto, CA (US)

( * ) Notice: Subject to any disclaimer, the term of this patent is extended or adjusted under 35 U.S.C. 154(b) by 844 days.

(21) Appl. No.: 16/869,312

(22) Filed: May 7, 2020

(65) Prior Publication Data

US 2021/0052553 A1  Feb. 25, 2021

Related U.S. Application Data

(62) Division of application No. 15/738,827, filed as application No. PCT/US2016/040566 on Jun. 30, 2016, now Pat. No. 10,688,083.

(60) Provisional application No. 62/187,061, filed on Jun. 30, 2015.

(51) Int. Cl.
| | | |
|---|---|---|
| *A61K 45/06* | (2006.01) | |
| *A61K 31/4184* | (2006.01) | |
| *A61K 31/4706* | (2006.01) | |
| *A61P 1/16* | (2006.01) | |
| *A61P 29/00* | (2006.01) | |
| *A61P 35/00* | (2006.01) | |
| *C07D 215/46* | (2006.01) | |
| *C07D 235/14* | (2006.01) | |

(52) U.S. Cl.
CPC ...... *A61K 31/4184* (2013.01); *A61K 31/4706* (2013.01); *A61K 45/06* (2013.01); *A61P 1/16* (2018.01); *A61P 29/00* (2018.01); *A61P 35/00* (2018.01); *C07D 215/46* (2013.01); *C07D 235/14* (2013.01)

(58) Field of Classification Search
CPC ................ A61K 31/4184; A61K 45/06; A61K 31/4706; A61P 1/16; A61P 29/00; A61P 35/00; C07D 215/46; C07D 235/14
USPC ....................................................... 514/313
See application file for complete search history.

(56) References Cited

U.S. PATENT DOCUMENTS

| | | | |
|---|---|---|---|
| 4,181,725 A | 1/1980 | Voorhees et al. | |
| 9,101,628 B2 | 8/2015 | Einav et al. | |
| 2004/0009949 A1 | 1/2004 | Krieg | |
| 2006/0014786 A1 | 1/2006 | Raut | |
| 2010/0028299 A1 | 2/2010 | Einav et al. | |
| 2010/0227847 A1 | 9/2010 | Broo et al. | |
| 2011/0104157 A1 | 5/2011 | Kinoshita et al. | |
| 2012/0082659 A1 | 4/2012 | Land et al. | |
| 2012/0114670 A1 | 5/2012 | Land et al. | |
| 2012/0117671 A1 | 5/2012 | Yoneyama et al. | |
| 2012/0202849 A1 | 8/2012 | Pareek et al. | |
| 2012/0276050 A1* | 11/2012 | Choong ............... | C07D 235/28 514/304 |
| 2013/0273003 A1 | 10/2013 | Koziel | |
| 2014/0073606 A1 | 3/2014 | Chu et al. | |
| 2015/0045349 A1 | 2/2015 | Nagamiya et al. | |

FOREIGN PATENT DOCUMENTS

| | | |
|---|---|---|
| CN | 101102760 A | 1/2008 |
| CN | 101193622 A | 6/2008 |
| CN | 101903026 A | 12/2010 |
| CN | 102046200 A | 5/2011 |
| CN | 102448458 A | 5/2012 |
| CN | 102548393 A | 7/2012 |
| CN | 103550242 A | 2/2014 |
| CN | 104271574 A | 1/2015 |
| CN | 105934438 A | 9/2016 |
| JP | 2007-509950 A | 4/2007 |
| JP | 2007-516217 A | 6/2007 |
| JP | 2009-526070 A | 7/2009 |
| JP | 2012-520884 A | 9/2012 |
| JP | 2014-097964 A | 5/2014 |
| JP | 2015-117185 A | 6/2015 |
| TW | 200902047 A | 1/2009 |
| WO | WO 98/17231 A2 | 4/1998 |
| WO | WO 00/66107 A2 | 11/2000 |
| WO | WO 2004/080445 A1 | 9/2004 |
| WO | WO 2006/131737 A2 | 12/2006 |
| WO | WO 2009/039246 A2 | 3/2009 |
| WO | WO 2011/041311 A2 | 4/2011 |
| WO | WO 2012/100248 A1 | 7/2012 |
| WO | WO 2013/177219 A1 | 11/2013 |
| WO | WO 2013/180149 A1 | 12/2013 |
| WO | WO 2014/031769 A2 | 2/2014 |
| WO | WO 2015/081133 A2 | 6/2015 |

OTHER PUBLICATIONS

Masuzaki, R. et al., "Does chemotherapy prevent HCV-related hepatocellular carcinoma? Pros," Digestive and Liver Disease, vol. 42, Jun. 30, 2010, pp. S281-S286.

Dvory-Sobol, H. et al., "The Future of HCV Therapy: NS4B as an Antiviral Target," Viruses, vol. 2, Issue 11, Nov. 2010, pp. 2481-2492.

Japan Patent Office, Notice of Reasons for Refusal, JP Patent Application No. 2017-568408, May 25, 2020, ten pages.

Brandes, L.J. et al., "Enhanced Cancer Growth in Mice Administered Daily Human-Equivalent Doses of Some $H_1$-Antihistamines: Predictive In Vitro Correlates," Journal of the National Cancer Institute, vol. 86, No. 10, May 18, 1994, pp. 770-775.

Lamas, D.J.M. et al., "Therapeutic potential of histamine $H_4$ receptor agonists in triple-negative human breast cancer experimental model," British Journal of Pharmacology, vol. 170, Feb. 2013, pp. 188-199.

(Continued)

*Primary Examiner* — Yevgeny Valenrod
(74) *Attorney, Agent, or Firm* — Fenwick & West LLP

(57) ABSTRACT

Disclosed herein are methods for use of clemizole for the treatment of a subject in need thereof. Uses include methods of treating inflammatory conditions. Uses also include methods of treating non-alcoholic steatohepatitis in a subject.

25 Claims, 8 Drawing Sheets

(56) References Cited

OTHER PUBLICATIONS

Olsson, H.L. et al., "Effects of antihistamine use on survival in breast cancer," Journal of Clinical Oncology, vol. 36, Iss. 15, Jun. 1, 2018, pp. 1-2 (abstract only).
Bielen, R. et al., "The risk of early occurrence and recurrence of hepatocellular carcinoma in hepatitis C-infected patients treated with direct-acting antivirals with and without pegylated interferon: A Belgian experience," Journal of Viral Hepatitis, vol. 24, May 2, 2017, pp. 976-981.
Blaya, B. et al., "Histamine and histamine receptor antagonists in cancer biology," Inflammation & Allergy-Drug Targets 9(3), 2010, pp. 146-157.
Cardenas, L. et al., "Treatment of circular movement auricular flutter (the use of an antihistaminic: clemizole)," Arch Mal Coeur Vaiss 62(3), Mar. 3, 1969, pp. 401-411.
Cardoso, H. et al., "High incidence of hepatocellular carcinoma following successful interferon-free antiviral therapy for hepatitis C associated cirrhosis," Journal of Hepatology, Letters to the Editor, vol. 65, Iss. 5, Nov. 2016, pp. 1070-1071.
China National Intellectual Property Administration, Office Action, CN Patent Application No. 201680039155.3, Dec. 18, 2019, 11 pages (with concise explanation of relevance).
Einav, S. et al., "Discovery of a hepatitis C target and its pharmacological inhibitors by microfluidic affinity analysis," Nat Biotechnol 26(9), Sep. 2008, pp. 1019-1027.
Einav, S. et al., "The Hepatitis C Virus (HCV) NS4B RNA Binding Inhibitor Clemizole is Highly Synergistic with HCV Protease Inhibitors," The Journal of Infectious Diseases, vol. 202, Iss. 1, Jul. 1, 2010, pp. 65-74.
El-Serag, H.B., "Hepatocellular Carcinoma," The New England Journal of Medicine, vol. 365, Issue 12, Sep. 22, 2011, pp. 1118-1127.
European Patent Office, Extended European Search Report and Opinion, EP Patent Application No. 16818845.6, Apr. 10, 2019, 19 pages.
European Patent Office, Partial Supplemental European Search Report, EP Patent Application No. 16818845.6, Dec. 20, 2018, 16 pages.
Finkelstein, M. et al., "Some Aspects of the Pharmacology of Clemizole Hydrochloride," Journal of the American Pharmaceutical Association, vol. 49, Iss. 1, Jan. 1960, pp. 18-22.
Fujii, M. et al., "A murine model for non-alcoholic steatohepatitis showing evidence of association between diabetes and hepatocellular carcinoma," Medical Molecular Morphology, vol. 46, Feb. 22, 2013, pp. 141-152.
Fujikawa, T. et al., "Cimetidine inhibits epidermal growth factor-induced cell signaling," Journal of Gastroenterology and Hepatology 22(3), Mar. 2007, pp. 436-443.
Furst, D.E., "Pharmacokinetics of Hydroxychloroquine and Chloroquine During Treatment of Rheumatic Diseases," 1996, Lupus, Vo. 5., No. 1, Supplemental pp. S11-S15; Abstract, p. S11, para (4), p. S12, paras [2]-[6], p. S13 para [4].
Jacques, A. et al., "Clinical Evaluation of Clemizole in Allergic Rhinitis," Int. Rec. Med. 1960, vol. 173, No. 2, Jan. 1, 1960, pp. 88-91.
Jangi, S.M. et al., "H1 histamine receptor antagonists induce genotoxic and caspase-2-dependent apoptosis in human melanoma cells," Carcinogenesis 27(9), Mar. 28, 2006, pp. 1787-1796.
Jesuino De Oliveria Andrade, J. et al., "Association Between Hepatitis C and Hepatocellular Carcinoma," J. Glob. Infect. Dis1(1), Jan.-Jun. 2009, pp. 33-37.
Kiang, T. K. L. et al., "Telaprevir: Clinical Pharmacokinetics, Pharmacodynamics, and Drug-Drug Interactions," Clin Pharmacokinet, vol. 52, Apr. 4, 2013, pp. 487-510.
Kozbial, K. et al., "Unexpected high incidence of hepatocellular carcinoma in cirrhotic patients with sustained virologic response following interferon-free direct-acting antiviral treatment," Journal of Hepatoloqv, Letters to the Editor, vol. 65, Iss. 4, Oct. 2016, pp. 856-858.
Lefebvre, E. et al., "Anti-fibrotic and anti-inflammatory activity of the dual CCR2 and CCR5 antagonist cenicriviroc in a mouse model of NASH." Hepatology, vol. 58, Oct. 2013, pp. 221A-222A.
Llovet, J.M. et al., "Sorafenib in Advanced Hepatocellular Carcinoma," The New England Journal of Medicine, vol. 359, Jul. 24, 2008, pp. 378-390.
Martin, R.K. et al., "Mast cell histamine promotes the immunoregulatory activity of myeloid-derived suppressor cells," Journal of Leukocyte Biology, vol. 96, Jul. 2014, pp. 151-159.
Meretey, K. et al., "Histamine influences the expression of the interleukin-6 receptor on human lymphoid, monocvtoid and hepatoma cell lines." Agents and Actions, vol. 33, Iss. 1-2, May 1991, pp. 189-191.
Nakagawa, H., "Recent advances in mouse models of obesity- and nonalcoholic steatohepatitis-associated hepatocarcinogenesis," World Journal of Hepatology, vol. 7, Iss. 17, pp. 2110-2118, Y=2015.
PCT International Search Report and Written Opinion, International Application No. PCT/US2016/040566, dated Nov. 3, 2016, 39 pages.
Ray, E. M. et al., "Optimal therapy for patients with hepatocellular carcinoma and resistance or intolerance to sorafenib: challenges and solutions," Journal of Hepatocellular Carcinoma, Nov. 8, 2017, pp. 131-138.
Reig, M. et al., "Unexpected high rate of early tumor recurrence in patients with HGV-related HCC undergoing interferon-free therapy," Journal of Hepatology, vol. 65, Iss. 4, Oct. 2016, pp. 719-726.
Schofer, H. "Syphilis treatment. German and international guidelines—a comparison," Hautarzt 56(2), Feb. 2005, pp. 141-150.
Singal, A. G. et al., "Direct-Acting Antiviral Therapy Not Associated with Recurrence of Hepatocellular Carcinoma in a Multicenter North American Cohort Study," Gastroenterology, vol. 156, No. 6, May 2019, pp. 1683-1692.
Taiwan Intellectual Property Office, Office Action, TW Patent Application No. 105120868, Feb. 27, 2020, seven pages (with English translation of search report).
United States Office Action, U.S. Appl. No. 15/738,827, filed Jan. 28, 2020, ten pages.
United States Office Action, U.S. Appl. No. 15/738,827, filed Jun. 19, 2019, ten pages.

* cited by examiner

The Structure of Hydroxychloroquine (rac-1) and R-hydroxychloroquine rac-1

(R)-1

Inhibition of tumor formation by compound D

| Group | Mouse ID | Number visible tumor nodules | Maximum diameter of visible tumor nodules (mm) | Mean number visible tumor nodules | Mean maximum diameter of visible tumor nodules (mm) |
|---|---|---|---|---|---|
| Vehicle | 101 | 3 | 14.4 | 3.0 ± 2.0 | 7.3 ± 6.5 |
|  | 102 | 5 | 5.4 |  |  |
|  | 111 | 1 | 2.0 |  |  |
| Compound D | 501 | 0 | 0.0 | 0.3 ± 0.6 | 0.7 ± 1.2 |
|  | 505 | 1 | 2.0 |  |  |
|  | 510 | 0 | 0.0 |  |  |

Posterior left lobe—vehicle control    Posterior left lobe—compound D treated

USE OF CLEMIZOLE COMPOUNDS FOR TREATMENT OF INFLAMMATORY CONDITIONS

CROSS REFERENCE TO RELATED APPLICATIONS

This application is a divisional of U.S. patent application Ser. No. 15/738,827 filed on Dec. 21, 2017, which is a national stage application, filed under 35 U.S.C. § 371, of International Patent Application No. PCT/US2016/040566, filed on Jun. 30, 2016, which claims the benefit of U.S. Provisional Patent Application No. 62/187,061, filed on Jun. 30, 2015, each of which is incorporated by reference herein in its entirety.

STATEMENT REGARDING FEDERALLY SPONSORED RESEARCH OR DEVELOPMENT

This invention was made with government support under R42 AI088793/NIAID NIH HHS/United States awarded by the National Institute of Health and National Institute of Allergy and Infectious Disease. The government has certain rights in the invention.

FIELD OF THE INVENTION

The present invention is directed to the field of medicine and more specifically to the use of certain compounds for the treatment and prevention of inflammatory and cancerous conditions, especially in liver.

BACKGROUND

Treatment and prevention of inflammatory and cancerous conditions represent large, unmet medical need. Inflammatory conditions in liver such as non-alcoholic steatohepatitis (NASH), in particular require improved therapies. Left untreated, NASH and other inflammatory liver disorders, such as those arising from viral infections, can lead to hepatocellular carcinoma. The present invention addresses these needs by providing methods for treatment and/or prevention of inflammatory and/or cancerous conditions as described below.

SUMMARY

Disclosed herein is a method comprising administrating an effective amount of clemizole and/or cholorquine, or an analog thereof, to a subject in need thereof. In some aspects of the invention, subjects are administered either R-chloroquine, clemizole or R-chloroquine in combination with clemizole.

In some aspects of the invention, the subject has an inflammatory condition.

In other aspects of the invention, the subject has an inflammatory liver condition. In some aspects of the invention, the subject has non-alcoholic steatohepatitis, and wherein the method further comprises treating non-alcoholic steatohepatitis. In some aspects, the method reduces lobular inflammation of the liver. In other aspects, the method reduces the risk of liver cancer. In yet other aspects of the invention, the subject has liver cancer, and wherein the method further comprises treating liver cancer.

In some aspects of the invention clemizole and/or R-chloroquine is administered to a subject with non-alcoholic steatohepatitis. In other aspects, the administration of clemizole or R-chloroquine to a subject results in reduced levels plasma alanine aminotransferase compared to vehicle controls. In other aspects, the administration of clemizole and/or R-chloroquine to a subject results in a reduced non-alcoholic fatty liver disease activity score as determined by histological analyses of liver tissue. In some aspects, the administration of clemizole and/or R-chloroquine results in reduced steatosis. In other aspects, the administration of clemizole and/or R-chloroquine results in reduced hepatocyte ballooning. In yet other aspects, the administration of clemizole and/or R-chloroquine results in reduced lobular inflammation.

In some aspects of the invention, clemizole and/or R-chloroquine is administered to a subject to reduce the risk of development of liver cancer. In other aspects of the invention, the subject has been diagnosed with non-alcoholic steatohepatitis. In other aspects of the invention, clemizole and/or R-chloroquine is administered to a subject suffering from liver cancer. In yet other aspects, the administration of clemizole and/or R-chloroquine results in reduced tumor burden in the subject or increased survival of the subject.

In some aspects of the invention, 0.5-50 mg/kg of clemizole is administered to a subject. In some aspects, clemizole is administered once daily, twice daily or thrice daily. In other aspects, clemizole is administered daily for 1, 2, 3, 4, 5, 6 or more weeks.

In some aspects of the invention 0.5-50 mg/kg of R-chloroquine is administered to a subject. In other aspects, R-chloroquine is administered once daily, every other day or weekly. In some aspects, R-chloroquine is administered for 1, 2, 3, 4, 5, 6 or more weeks. In yet other aspects, R-chloroquine is administered as a double loading dose daily for the first two days of treatment, followed by a single dose which is half of the double loading dose for the remainder of the treatment.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 3 illustrates the synthetic scheme for the good manufacturing practice (GMP) synthesis of clemizole.

DETAILED DESCRIPTION

Advantages and Utility

Briefly, and as described in more detail below, described herein are compositions and methods for treating nonalcoholic steatohepatitis or reducing the risk or severity of liver cancer using clemizole and/or R-chloroquine. The advantages for this approach include, but are not limited to, reduction of inflammation in a subject suffering from an inflammatory condition, reduction of lobular inflammation of the liver, improved liver function, and reduced risk of development or progression of liver cancer when patients are treated with clemizole and/or R-chloroquine than patients not treated with clemizole and/or R-chloroquine.

Definitions

Terms used in the claims and specification are defined as set forth below unless otherwise specified.

The term, "treatment" refers to any therapeutically beneficial result in the treatment of a disease state, e.g., a disease state caused by inflammatory liver conditions, including prophylaxis, lessening in the severity or progression, remission, or cure thereof.

The term "in situ" refers to processes that occur in a living cell growing separate from a living organism, e.g., growing in tissue culture.

The term, "in vivo" refers to processes that occur in a living organism.

The term "mammal" as used herein includes both humans and non-humans and include but is not limited to humans, non-human primates, canines, felines, murines, bovines, equines, and porcines.

The term, "effective amount" means an amount sufficient to produce a desired effect, e.g., an amount sufficient to prevent liver cancer or reduce the amount of liver cancer in a subject.

The term, "subject" refers to cells, human and non-human animals.

The term, "therapeutically effective amount" is an amount that is effective to ameliorate a symptom of a disease. A therapeutically effective amount can be a "prophylactically effective amount" as prophylaxis can be considered therapy.

The term, "administration" refers to introducing an agent of the present disclosure into a host. One preferred route of administration of the agents is oral administration. Another preferred route is intravenous administration. However, any route of administration, such as topical, subcutaneous, peritoneal, intra-arterial, inhalation, vaginal, rectal, nasal, introduction into the cerebrospinal fluid, or instillation into body compartments can be used.

The term, "vehicle control" broadly refers to any inert medium in which the active ingredient is administered, including but not limited to solvents, carriers or binders for the active ingredient.

The term, "deuterated analog" refers to modified versions or analogs of the compounds of the invention where the compound contains at least one deuterium isotope.

Figure 1:
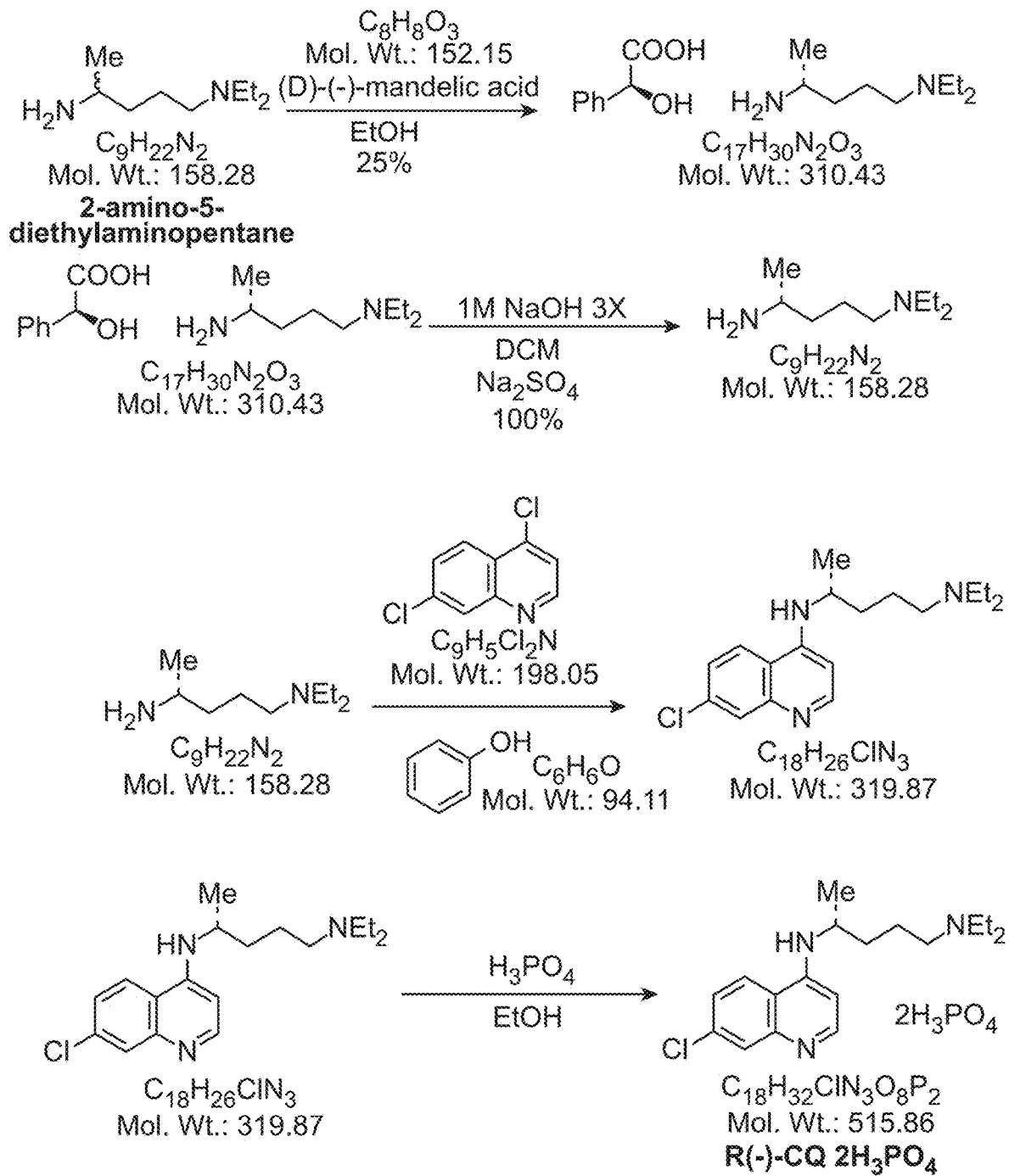
FIG. 1: A scheme for the process of synthesis of R-chloroquine is illustrated.

The term, "clemizole metabolite" refers to the clemizole metabolite compounds, M1, M12 and M14, as described in FIG. 1 of the instant application.

Figure 6:
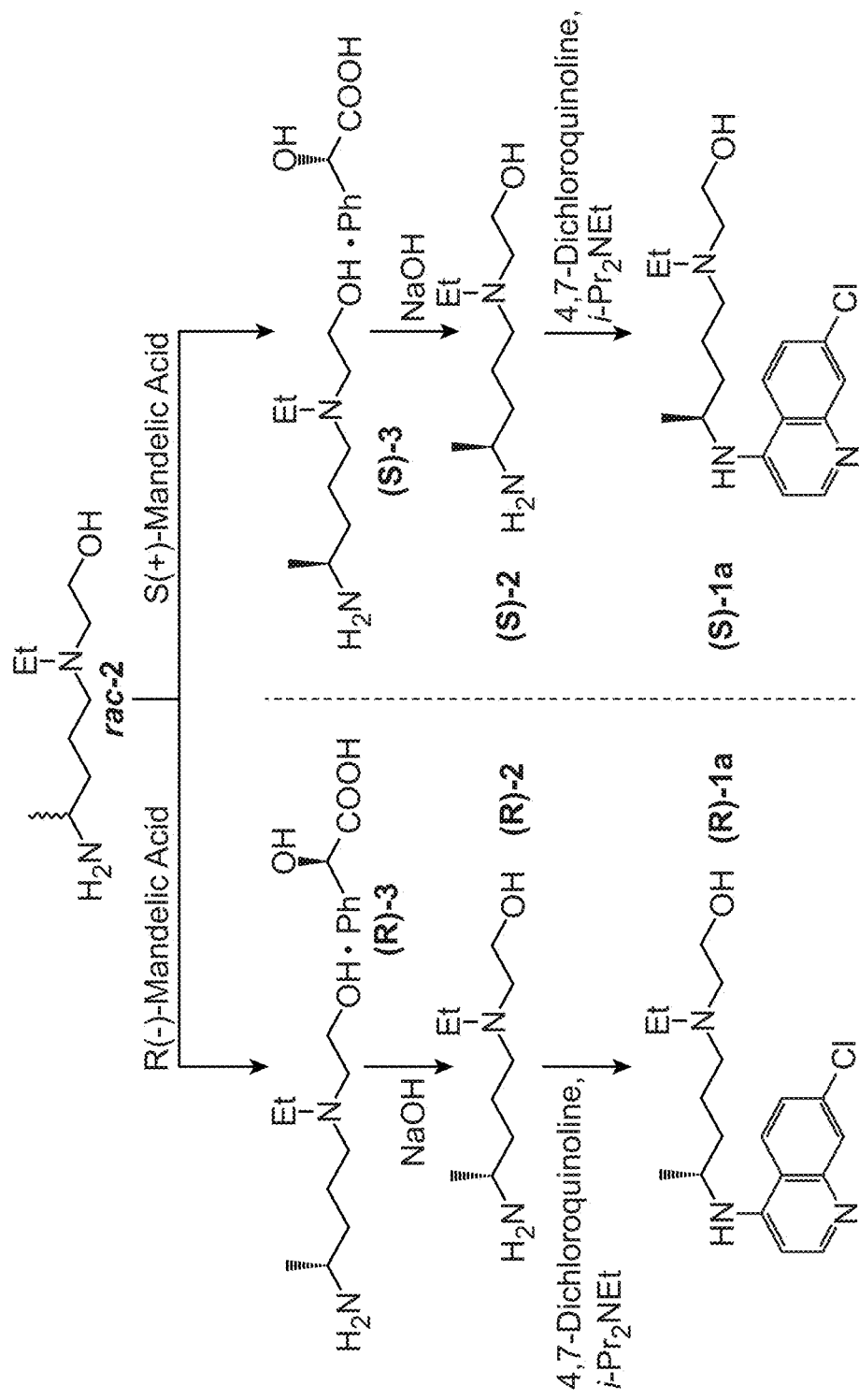
FIG. 6: A scheme for the process of synthesis of enantiomers of hydroxychloroquine is illustrated.

The term, "R-chloroquine metabolite" refers to the metabolite compounds of chloroquine as described in FIG. 6 of the instant application.

Figure 7:
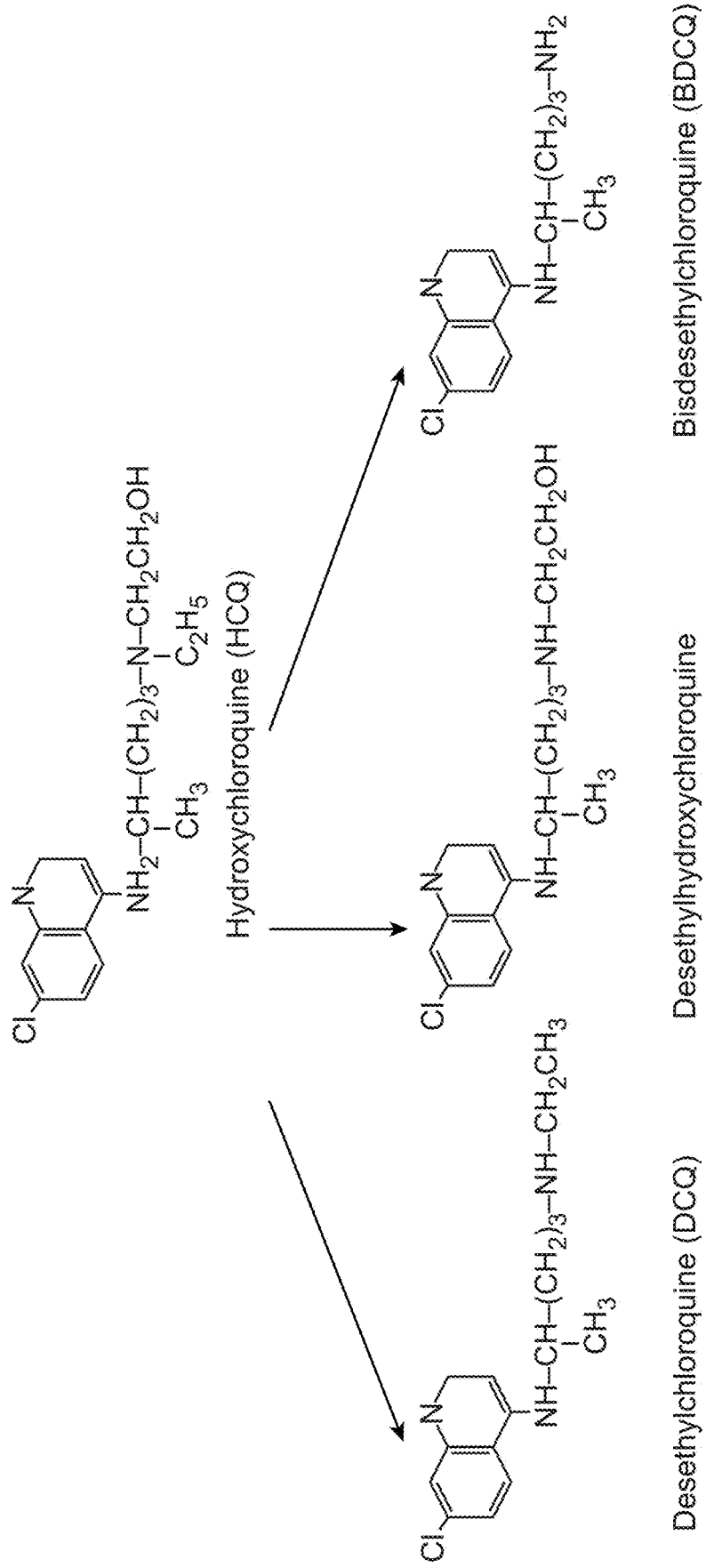
FIG. 7: The chemical structures of hydroxychloroquine metabolites are shown.

The term, "R-hydroxychloroquine metabolite" refers to the metabolite compounds of hydroxychloroquine, as described in FIG. 7 of the instant application.

The term, "anti-NASH agent" refers to drugs or compounds that are used to treat non-alcoholic steatohepatitis or conditions associated with non-alcoholic steatohepatitis which include, but are not limited to, FXR agonists (e.g. obeticholic acid and PX-104), LOXL2 inhibitors (e.g. Simtuzumab), caspase protease inhibitors (e.g. Emricasan and icosapent ethyl ester), cysteamine bitartrate (e.g. Proscysbi or RP103), galectin-3 inhibitors (e.g. GR-MD-02 and LJPC-1010), CCR2 and CCR5 pathway inhibitors (e.g. Cenicriviroc), PPAR agonists (e.g. GFT505, DUR-928, Saroglitazar and Pioglitazone), cysteine depleting agents (e.g. RP103), SGLT-2 inhibitors (e.g. remogliflozin etabonate), GLP-1 (e.g. liraglutide), bile acids (Ursodeoxycholic acid), synthetic fatty acid and bile acid conjugates (e.g. Aramchol), Sirtuin stimulants (e.g. MB 12066), Apoptosis signal-regulating kinase 1 (ASKI) inhibitors (e.g. GS-4997) and immunomodulators (e.g. IMM124E).

As used herein, the term, "inflammatory condition" refers to medical problems that are directly caused by inflammatory cytokines or cells involved in inflammation. Inflammatory conditions, include, but are not limited to, non-alcoholic steatohepatitis, arthritis where inflammatory cytokines destroy and lead to lesions in the synovial membrane and destruction of joint cartilage and bone; kidney failure where inflammatory cytokines restrict circulation and damage nephrons; lupus wherein inflammatory cytokines induce an autoimmune attack; asthma where inflammatory cytokines close the airway; pulmonary arterial hypertension where inflammatory cytokines induce an elevation of the pulmonary arterial pressure; psoriasis where inflammatory cytokines induce dermatitis; pancreatitis where inflammatory cytokines induce pancreatic cell injury; allergy where inflammatory cytokines induce autoimmune reactions; fibrosis where inflammatory cytokines lead to traumatized tissue; surgical complications where inflammatory cytokines prevent healing; anemia where inflammatory cytokines interfere with erythropoietin production; and fibromyalgia where inflammatory cytokines are elevated in fibromyalgia patients. Other diseases associated with chronic inflammation include cancer, which is caused by chronic inflammation; heart attack where chronic inflammation contributes to coronary atherosclerosis; Alzheimer's disease where chronic inflammation destroys brain cells; congestive heart failure where chronic inflammation causes heart muscle wasting; stroke where chronic inflammation promotes thrombo-embolic events; and aortic valve stenosis where chronic inflammation damages heart valves. Arteriosclerosis, osteoporosis, Parkinson's disease, infection, inflammatory bowel disease including Crohn's disease and ulcerative colitis as well as multiple sclerosis (a typical autoimmune inflammatory-related disease) are also related to inflammation. Some diseases in advanced stages can be life threatening. Several methodologies are available for the treatment of such inflammatory diseases; the results, however, are generally unsatisfactory as evidenced by a lack of efficacy and drug related side effects associated therewith.

As used herein, the term "non-alcoholic fatty liver disease activity score" refers to the results of histological examination of liver tissue whereby the tissue has been examined for steatosis, hepatocyte ballooning and/or lobular inflammation.

As used herein, the term "liver cancer" refers to hyperproliferative diseases of the liver, including, but not limited to, hepatocellular carcinoma, fibrolamellar hepatocellular carcinoma, cholangiocarcinoma, angiosarcoma, secondary or metastatic liver cancer and hepatoblastoma.

As used herein, the term "chemotherapeutic agents" refers to compounds that can be useful in the treatment of disease (e.g., cancer). Chemotherapy agents of the present invention can include any suitable chemotherapy drug or combinations of chemotherapy drugs (e.g., a cocktail). Exemplary chemotherapy agents include, without limitation, alkylating agents, platinums, anti-metabolites, anthracyclines, taxanes, camptothecins, nitrosoureas, EGFR inhibitors, antibiotics, HER2/neu inhibitors, angiogenesis inhibitors, kinase inhibitors (e.g. sorafenib), proteasome inhibitors, immunotherapies, hormone therapies, photodynamic therapies, cancer vaccines, histone deacetylase inhibitors, sphingolipid modulators, oligomers, other unclassified chemotherapy drugs and combinations thereof. Exemplary chemotherapeutic agents affective against cancer also include, without limitation, daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, taxotere, vincristine, vinblastine, etoposide, teniposide, cisplatin and diethylstilbestrol (DES).

The term, a "pharmaceutically acceptable excipient," "pharmaceutically acceptable diluent", "pharmaceutically acceptable carrier", or "pharmaceutically acceptable adjuvant", means an excipient, diluent, carrier, and/or adjuvant that are useful in preparing a pharmaceutical composition that are generally safe, non-toxic and neither biologically or otherwise undesirable, and include an excipient, diluent, carrier, and adjuvant that are acceptable for veterinary use and or human pharmaceutical use. "A pharmaceutically acceptable excipient, diluent, carrier, and/or adjuvant" as used in the specification and claims includes one or more of such excipients, diluents, carriers and adjuvants.

"Pharmaceutically acceptable salt" refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. The term, "pharmaceutically acceptable salt" also refers to the compounds that can be combined with free chloroquine base (e.g. phosphate and diphosphate).

In the event that embodiments of the disclosed agents form salts, these salts are within the scope of the present disclosure. Reference to an agent of any of the formulas herein is understood to include reference to salts thereof, unless otherwise indicated. The term "salt(s)", as employed herein, denotes acidic and/or basic salts formed with inorganic and/or organic acids and bases. In addition, when an agent contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation.

The term "pharmaceutical composition" as used herein, is meant to encompass a composition suitable for administration to a subject, such as a mammal, especially a human. In general, "a pharmaceutical composition" is sterile, and preferably free of contaminants that are capable of eliciting an undesirable response within the subject.

The term "prodrug" refers to an inactive precursor of an agent that is converted into a biologically active form in vivo. The compounds of the invention include modified versions of R-chloroquine and clemizole, deuterated clemizole or clemizole metabolites that act as prodrugs. Examples of modifications of the compounds of the invention that could be used to produce prodrugs include, but are not limited to, the addition of esters, glycosides (sugar derivatives) or addition or removal of other nontoxic chemical groups that are enzymatically altered during metabolism in vivo (e.g., phosphorylation, dephosphorylation, dealkylation, dehydroylation or modification of sugar derivatives). Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

Abbreviations

Abbreviations used in this application include the following: It must be noted that, as used in the specification and the appended claims, the singular forms "a," "an" and "the" include plural referents unless the context clearly dictates otherwise.

Compound A=Recemic mixture of R-chloroquine and S-chloroquine
Compound B=R-chloroquine
Compound C=S-chloroquine
Compound D=clemizole
ALT=Alanine aminotransferase
HE=Hematoxylin and eosin
HFD=High fat diet
NAFLD=Nonalcoholic fatty liver disease
NASH=Non-alcoholic steatohepatitis
SD=Standard deviation
SPF=Specific pathogen-free
STZ=Streptozotocin Compounds of the Invention The formula for R-chloroquine and the process of synthesis of R-chloroquine is described in FIG. 1. Alternatively, R-chloroquine is commercially available and can be purchased from Chemical Entities of Biological Interest (ChEBI™); (catalog number, CHEBI: 48811).

Figure 2:
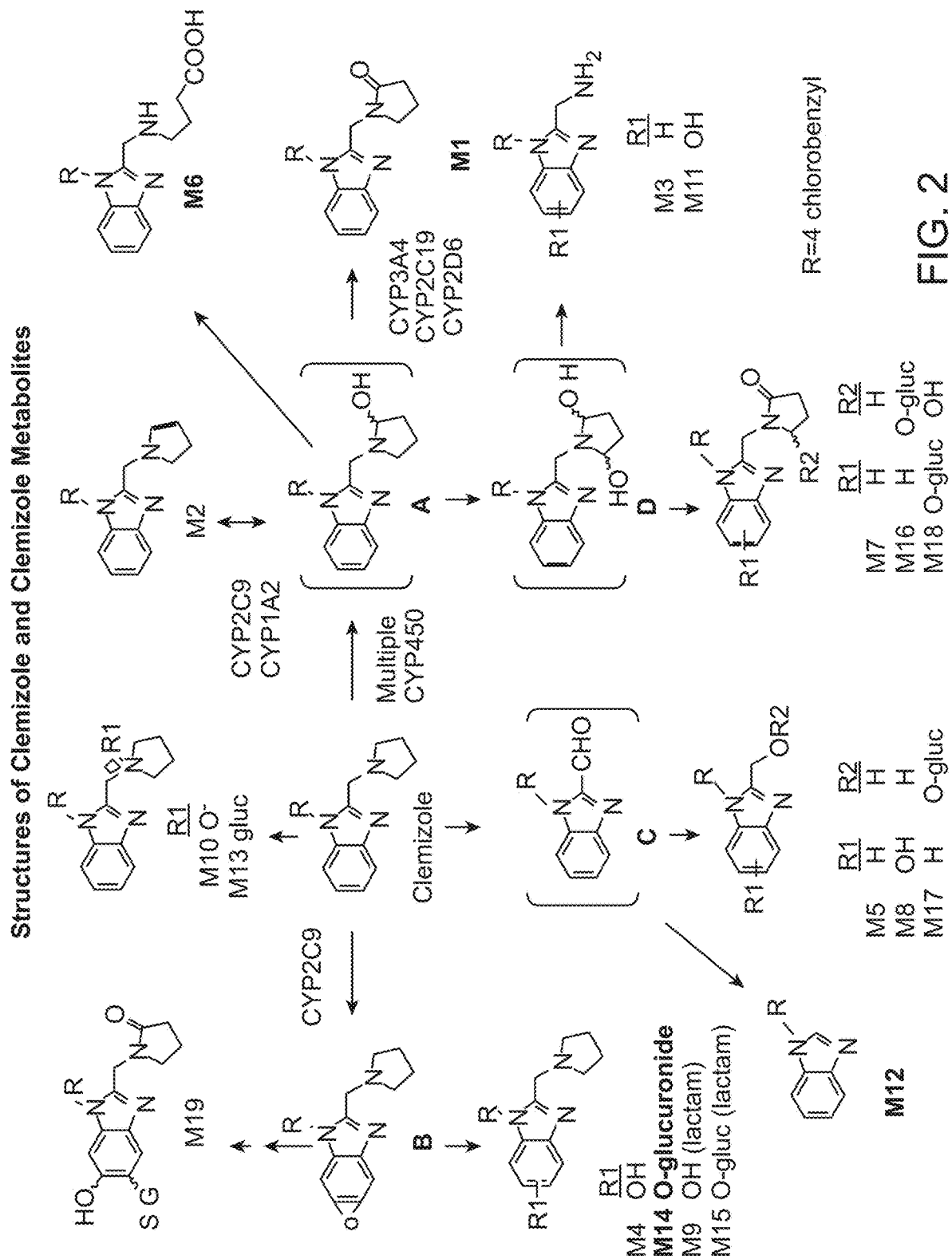
FIG. 2: The chemical structures of clemizole and clemizole metabolites are shown.

The structures of clemizole and the major human (M1, M6) and rodent (M12, M14) clemizole metabolites are shown in FIG. 2. Clemizole hydrochloride is commercially available from APExBIO™ (Catalog No. A3316).

Inhuman liver, clemizole is primarily converted to an intermediate A, which several CYP450 enzymes (CYP3A4, CYP2C19 or CYP2D6) can oxidize to ML. In the presence of CYP2C9 or CYP1A2, M2 is generated, but they cannot produce M1. Cyp2C9 appears to be the only source of M4, which is a minor metabolite in humans. CYP3A4, which is the most abundantly expressed CYP450 enzyme in human liver, mediates the majority of this drug biotransformation reaction. The ability of ritonavir, which is an inhibitor of CYP3A4 activity, to inhibit clemizole metabolism in vitro suggested that CYP3A4 plays a major role in clemizole metabolism in humans. In contrast, a different type (CYP2C-like) of aromatic oxidation reaction produces the rodent-predominant metabolites (M12, M14 and M15), through the dominant pathway for clemizole metabolism in rodent liver.

Synthesis of Clemizole Hydrochloride

Figure 3:
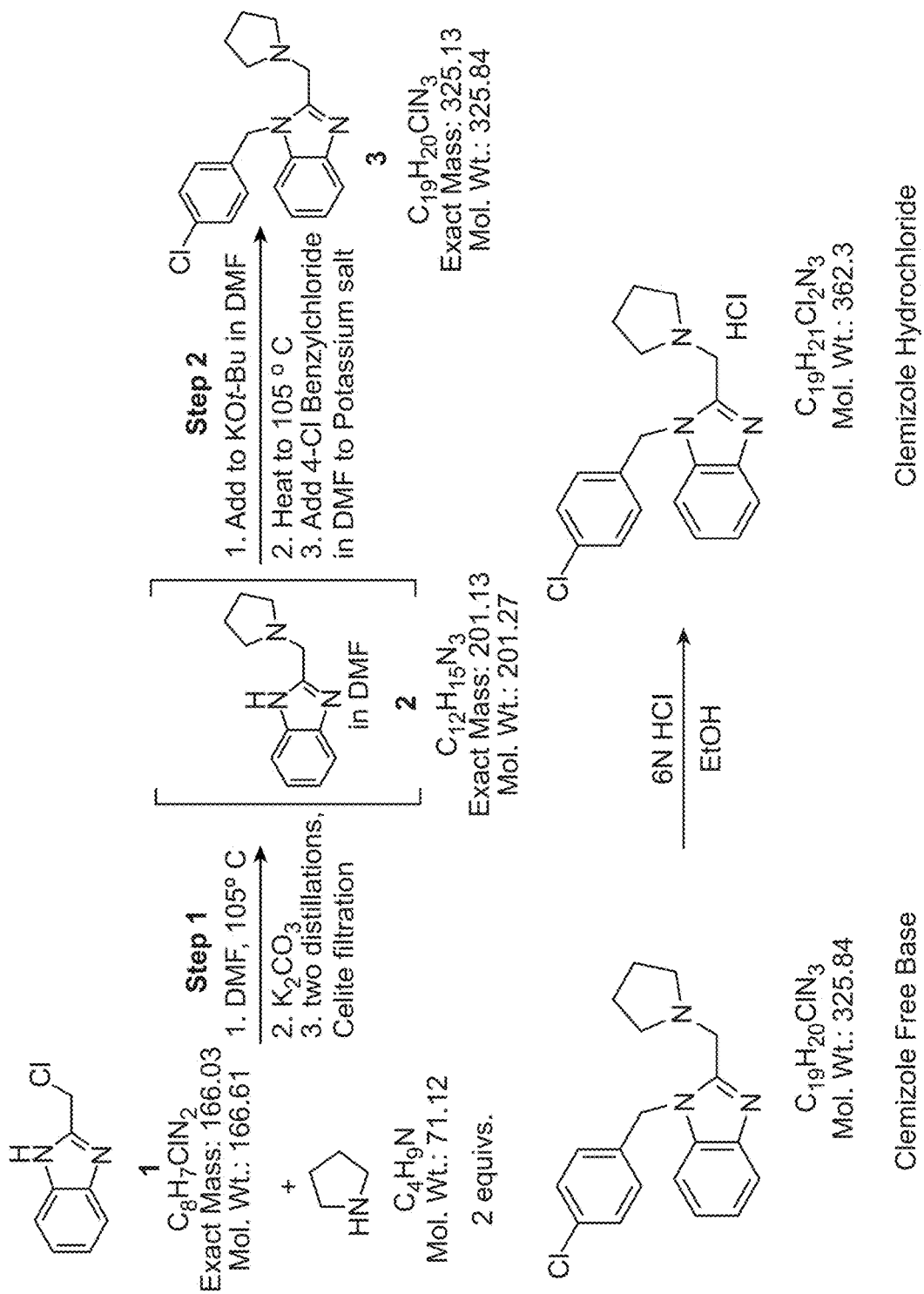
FIG. 3.
Figure 4:
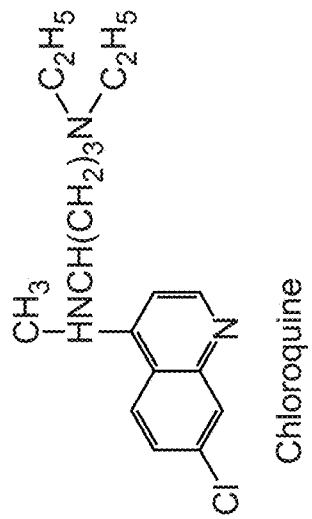
FIG. 4: The chemical structures of chloroquine metabolites are shown.
Figure 4:
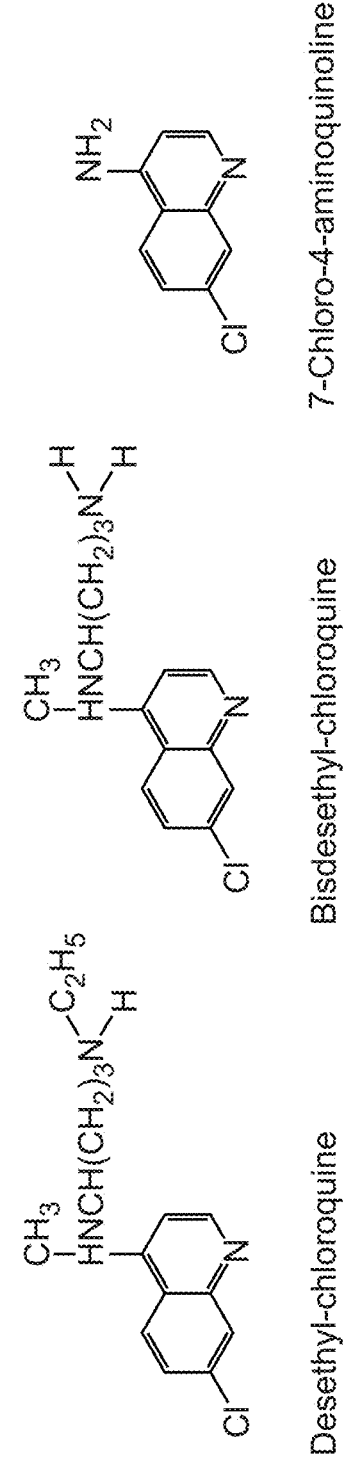
Figure 5:
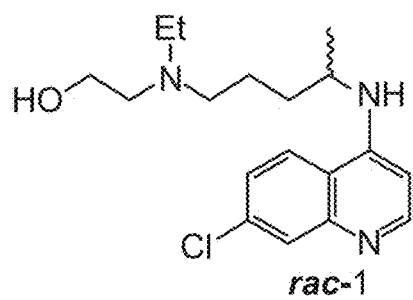
FIG. 5: The chemical structures of hydroxychloroquine (rac-1) and R-hydroxychloroquine is shown (R)-1.
Figure 5:
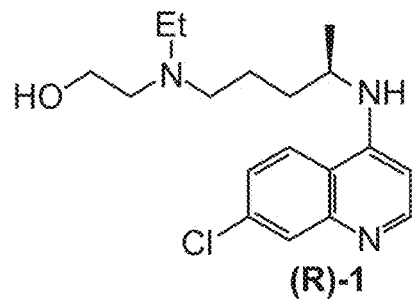

Clemizole hydrochloride is commercially available from APExBIO™ (Catalog No. A3316). FIG. 3 describes the synthetic scheme for the good manufacturing practice (GMP) production of clemizole. In certain embodiments, deuterated analogs of clemizole can be produced by substitution of a deuterated pyrorolidine for the pyrolidiane starting mater. Pyrrolidine-2,2,5,5-$d_4$ can be purchased from ©CDN Isotopes, Inc. (Product No. D-5946).

Fully substituted pyrrolidine, pyrrolidine-2,2,3,3,4,4,5,5-$d_8$ can be purchased from ©CDN Isotopes, Inc. (Product No. D-3532).

Synthesis of R-Chloroquine

As described in FIG. 1, (R)-(−)-chloroquine was prepared by condensing (R)-(−)-4-amino-1-(diethylamino)pentane with known 4,7-dichloroquinoline. The (R)-(−)-4-amino-1-(diethylamino)pentane was prepared by resolving known racemic (4-amino-1-(diethylamino)pentane via formation of a salt with known (D)-(−)-mandelic acid and separating the (D)-(−)-mandelic acid salts of the two enantiomers by crystallization.

Preparation of (R)-(−)-4-amino-1-(diethylamino) pentane

To a solution of (D)-(−)-mandelic acid (100 g, 658 mmol) in 350 mL ethyl alcohol was slowly added racemic 4-amino-1-(diethylamino)pentane (98 g, 658 mmol). The mixture was seeded with crystals of the (D)-(−)-mandelic acid salt of the title compound and, after standing overnight, the resulting solid was collected by filtration and rapidly washed two times with ice-cold ethanol to give the (D)-(−)-mandelic acid salt of the title compound as white crystals (Crop 1). The mother liquor was concentrated until cloudiness was observed, then reheated until a homogenous solution resulted. After seeding and standing overnight, the resulting solid was collected by filtration and rapidly washed two times with ice-cold ethanol to give a second crop of the desired salt as white crystals (Crop 2). The two salt crops (Crops 1 and 2) were combined to give a total of 44 g of the (D)-(−)-mandelic acid salt of the title compound. The above process was repeated 4 times. Multiple batches of the (D)-(−)-mandelic acid salt of the title compound (150 g in total) were combined and then dissolved in ethyl alcohol with heating and sonication. The solution was seeded and, after standing overnight, the resulting solid was collected by filtration and rapidly washed two times with ice-cold ethanol to give the (D)-(−)-mandelic acid salt of the title compound (Recrystallized Crop 1). The mother liquor was concentrated and the residue dissolved in ethyl alcohol with heating and sonication. The solution was then seeded and, after standing overnight, the resulting solid was collected by filtration to give a second crop of the (D)-(−)-mandelic acid salt of the title compound (Recrystallized Crop 2). The mother liquor was concentrated and the residue was dissolved in ethyl alcohol with heating and sonication. The solution was then seeded and, after standing overnight, the resulting solid was collected by filtration to give a third crop of the (D)-(−)-mandelic acid salt of the title compound (Recrystallized Crop 3). The three recrystallized crops (Recrystallized Crops 1, 2 and 3) were combined and dried in vacuo to give a total of 100 g of the (D)-(−)-mandelic acid salt of the title compound, $[\alpha]_D$=−56.2 (1% in $H_2O$). This salt was suspended in dichloromethane and washed three times with 1 M sodium hydroxide solution. The organic layer was dried ($Na_2SO_4$) and concentrated in vacuo to give the title compound, which was used directly in the next step.

Preparation of (R)-(−)-Chloroquine

A mixture of the crude (R)-(−)-4-amino-1-(diethylamino)pentane from above (approximately 45 g, 285 mmol, 1.00 equivalents), 4,7-dichloroquinoline (56 g, 285 mmol, 1.00 equivalents) and phenol (53.6 g, 570 mmol, 2.0 equivalents) was heated to 120° C. for 18 h, then cooled to room temperature and diluted with dichloromethane. The resulting mixture was washed with 1.5 M sodium hydroxide solution and the wash was back-extracted with dichloromethane. The combined organic layers were extracted with 1 M hydrochloric acid. The aqueous extract was basified to pH 12 with saturated sodium carbonate solution and extracted with dichloromethane. The organic extract was dried ($Na_2SO_4$) and concentrated in vacuo. The residue was then purified by column chromatography (silica gel eluting with 2.5% 7N $NH_3$/MeOH) to give 42.8 g of the title compound, $[\alpha]_D$=−101.3 (1% in EtOH).

This material was converted to its diphosphate salt by heating a solution of 42.8 g (133 mmol) of the title compound in ethyl alcohol to 90° C. for 15 min and adding dropwise two equivalents (314 g, 267 mmol) of 85% phosphoric acid. After heating the resulting suspension at reflux (90° C.) for 1 h and then cooling to room temperature, the solid was collected by filtration washed with ethanol and diethyl ether, and dried in vacuo to give 68 g of (R)-(−)-chloroquine diphosphate, $[\alpha]_D$=−82.96 (2.1% in $H_2O$).

$^1$H NMR (Methanol-d4): δ 8.59 (d, J=9.2 Hz, 1H), 8.36 (d, J=6.8 Hz, 1H), 7.92 (s, 1H), 7.61 (d, J=9.2 Hz, 1H), 6.89 (d, J=7.2 Hz, 1H), 4.05-4.14 (m, 1H), 3.07-3.17 (m, 6H), 1.73-1.96 (m, 4H), 1.39-1.41 (m, 3H) and 1.27-1.31 (m, 6H)

Synthesis and Purification of R-Hydroxychloroquine

The process for the synthesis and purification of enantiomers (R) and (S) hydroxychloroquine is fully described in Blaney, P. et al., "A Practical Synthesis of the Enantiomers of Hydroxychloroquine," Tetrahedron: Asymmetry, 1994, pp. 1815-1822, Vol. 5. A summary of this process has been included below.

As shown in FIG. 6, the racemic diamine rac-2 is resolved by crystallization of its salt with S(+)mandelic acid. Subsequent coupling with 4,7 dichloroquinoline gives S(+)-hydroxychloroquine ((S)-1a). Similarly, using the opposite enantiomer of mandelic acid gives (R)-2 and R(−)-hydroxychloroquine ((R)-1a). Resolution of (R)-2 and (S)-2 involves crystallization of its diastereomeric mandelate salts from iso-propanol. Using 0.5 molar equivalents of S(+)-mandelic acid and seeding the mixture with pure diastereomer at 45° C., 67% of (S)-3 is recovered after a single crystallization with a diastereomeric excess (d.e.) of 92%. Afterwards, (S)-3 or (R)-3 is hydrolyzed to the corresponding diamine (S)-2 or (R)-2. Ratios and yields are calculated without taking into account the presence of a variable quantity (up to 10%) of water in (S)-2 or (R)-2.

Preparation of S(+)-5-[N-Ethyl-N-(2-hydroxyethyl)amino]-2-pentanamine ((S)-2)

A solution of rac-2 (200 g, 1.15 mol) in 2-propanol (350 ml) was added to a solution of (+)-mandelic acid (87.4 g, 0.575 mol) in 2-propanol (500 ml). Additional 2-propanol was added to bring the total volume to 900 ml and the solution was stirred overnight at room temperature. Filtration gave white crystals (235 g) which were recrystallized twice more from 2-propanol (1800 rnJ and 1600 ml respectively) to afford (S)-3 (145.4 g) as white crystals. The solid was suspended in 35% aqueous sodium hydroxide (350 ml) and extracted with tert-butyl methyl ether (5×600 ml). The extracts were combined dried ($MgSO_4$) and concentrated to give (S)-2 (55.5 g, 55%) as a colorless oil. $^1$H NMR (CDCl3) δ 0.98 (3H, t, J=7.1 Hz), 1.025 (3H, d, J=6.3 Hz), 1.25-1.35 (2H, m), 1.35-1.55 (2H, m), ca. 1.9 (3H, brs), 2.42 (2H, t, J=7.3 Hz), 2.51 (2H, q, J=7.1 Hz), 2.54 (2H, t, J=5.5 Hz), 2.85 (1H, tq, J=6.3 and 5.2 Hz), 3.50 (2H, t, J=5.5 Hz); MS (CI, Ammonia) 175 ([MH]+). HRMS Calc. for $C_9H_{22}N_2O$: 175.181039; Found: 175.180493.

Preparation of R(−)-5-[N-Ethyl-N-(2-hydroxyethyl) amino]-2-pentanamine ((R)-2)

The mother liquor from the first crystallization above was concentrated. The residue was suspended in 35% aqueous sodium hydroxide (250 ml) and extracted with tert-butyl methyl ether (5×550 ml). The combined extracts were dried (MgSO$_4$) and concentrated to give a yellow oil (70.6 g). This was redissolved in 2-propanol (200 ml) and added to a solution of (−)-mandelic acid (64.00 g, 0.421 mol) in 2-propanol (300 ml). Additional 2-propanol was added to bring the total volume to 600 ml and the solution was stirred overnight at room temperature. Filtration gave white crystals (111 g) which were recrystallized twice more from 2-propanol (1100 ml and 800 ml respectively) to afford (R)-3 (77.2 g) as white crystals. $^1$H NMR DMSO-d$_6$) δ 0.92 (3H, t), 1.09 (3H, d), 1.35-1.55 (4H, m), 2.3-2.55 (6H, m), 3.03 (1H, tq). 3.43 (2H, t), 4.48 (1H, s), 7.1-7.25 (3H, m), 7.39 (2H, dd). (R)-3 was suspended in 35% aqueous sodium hydroxide (200 ml) and extracted with tert-butyl methyl ether (5×400 ml). The extracts were combined, dried (MgSO$_4$) and concentrated to give (R)-2 (29.3 g, 29%) as a colorless oil. $^1$NMR (CDCl3) δ 0.97 (3H, t, J=7.1 Hz), 1.025 (3H, d, J=6.3 Hz), 1.25-1.35 (2H, m), 135-1.5 (2H, m), ca 0.2.1 (3H, br s), 2.41 (2H, t. J=7.3 Hz), 2.51 (2H, q, J=7.1 Hz), 2.53 (2H, t, J=5.5 Hz), 2.85 (1H, tq, J=6.3 and 5.2 Hz), 3.49 (2H, t, J=5.5 Hz); HRMS (CLAmmonia) Calc. for $C_9H_{22}N_2O$: 175.181039; Found: 175.180390.

Preparation of S(+)-Hydroxychloroquine ((S)-1a)

A mixture of (S)-2 (55.47 g, 0.32 mol), 4,7dichloroquinoline (63.03 g, 0.32 mol) and diisopropylethylamine (63.9 ml, 0.37 mol) was heated at 125° C. under reflux in a nitrogen atmosphere for four days. After cooling, the mixture was transferred into a separating funnel using 1M aqueous sodium hydroxide (500 ml) and dichloromethane (500 ml). The organic phase was separated and the aqueous phase was re-extracted with dichloromethane (2×500 ml). The organic phases were combined, dried (MgSO$_4$) and concentrated to give a yellow oil (116 g) which was chromatographed on silica gel in 95:3:2 dichloromethane:triethylamine:methanol to give (S)-1a (73 g, 78%) as a pale yellow oil. Alternatively, the crude product was chromatographed on alumina in 2:2:1 acetone:hexane:methanol to give (S)-1a as a colourless oil. $^1$H NMR (CDCl$_3$) δ 0.99 (3H, t, J=7 Hz, CH$_2$CH$_3$), 1.285 (3H, d, J=6 Hz, CHCH$_3$), 1.45-1.85 (4H, m), 2.35-2.75 (6H, m), 3.4-3.95 (3H, m), 5.18 (1H, br d, J=8 Hz, NH), 6.37 (1H, d, J=6 Hz, 3-H), 7.28 (1H, dd, J$_o$=9 Hz, J$_m$=2 Hz, 6-H), 7.74 (1H, d, J=9 Hz, 5-H), 7.91 (1H, d, J=2 Hz, 8-H), 8.465 (1H, d, J=6 Hz, 2-H); $^{13}$C NMR (CDCl$_3$) 11.5 (CH$_2$CH$_3$), 20.2 (CH—CH$_3$), 23.9 (CH$_2$CH$_2$CH$_2$N), 34.2 (CH$_2$CH$_2$CH$_2$N). 47.5 (CH$_2$CH$_3$), 48.3 (CH), 53.1 (CH$_2$H2CH$_2$N), 54.9 (CH$_2$CH$_2$OH), 58.5 (CH$_2$CH$_2$OH), 99.0 (C3), 117.2 (C4a), 121.3 (C6), 125.0 (C8), 128.4 (C5), 134.7 (C7), 149.1 (C4), 151.65 (C2); MS (EI, 70EV) 337.335 (15.44%, M$^+$), 306.304 (20.62%, [M-CH$_2$OH]$^+$), 247 (81%), 102 (100%); HRMS Calc, for $C_{18}H_{26}ClN_3O$: 335.176440; Found: 335.175518

Preparation of R(-Hydroxychloroquine ((R)-1a)

A mixture of (R)-2 (29.34 g, 0.168 mol), 4,7-dichloroquinoline (33.34 g, 0.168 mol) and diisopropylethylamine (33.8 ml, 0.194 mol) was heated at 135° C. under reflux in a nitrogen atmosphere for three days. Work-up and purification as described for (S)-1a gave (R)-1a (39.8 g, 84%) as a pale yellow oil. Alternative Purification: crude (R)-1a (18.7 g) was dissolved in hydrochloric acid (1M, 50 ml) and washed with ethyl acetate (2×50 ml) to remove 2,7dichloroquinoline. After neutralization to pH 7.5 with 1M aqueous sodium hydroxide, the aqueous phase was washed again with ethyl acetate (2×50 ml), then stirred overnight with activated charcoal. After filtration through celite, the mixture was basified to pH 12 and extracted with ethyl acetate (4×50 ml). The extracts were combined, dried (MgSO$_4$) and concentrated to give (R)-1a as a pale yellow oil (17.2 g). $^1$H NMR (CDCl$_3$) δ0.99 (3H, t). 1.285 (3H, d), 1.45-1.85 (4H, m), 2.35-2.75 (6H, m), 3.4-3.95 (3H, m), 5.18 (1H, brd), 6.37 (1H, d), 7.28 (1H, dd), 7.74 (1H, d), 7.91 (1H, d), 8.465 (1H, d); $^{13}$C NMR (CDCl$_3$) δ 11.5, 20.2, 23.9, 34.2, 47.5, 48.3, 53.1, 54.9, 58.5, 99.0, 117.2, 121.3, 125.0, 128.4, 134.7, 149.1, 151.65; MS (thermospray) 338, 336 ([MH]+); major fragment ions at 247 (100%, [M-EtNHCH$_2$CH$_2$OH]$^+$), 158.

The Procedure for Assaying the Enantiomeric Purities of (R)-2 and (S)-2

Fully resolved (R)-2 or (S)-2 has an $[\alpha]_D$ in the region of 6. Reliable methods for determining enantiomeric purity involve $^1$H-NMR of diastereomeric derivatives of (R)-2 and (S)-2. The result of addition of one molar equivalent of (R)-α-methoxy-α-trifluoromethylphenylacetic acid (MTPA) to chloroform solutions of (R)-2 and (S)-2 causes resonances due to H$^a$ in the two diastereomers to broaden and move to higher frequency, while excess MTPA forms diastereomeric salts in which the resonances due to H$^a$ and H$^b$ change position. In the latter case, there is a large separation between the resonances due to H$^b$ of the two diastereomers. This technique allows detection of as little as 1% of the minor enantiomer. It is suggested that monoprotonation gives a species which exists in a pseudocyclic form, whereas the diprotonated species exists in an acyclic form. Similarly, in the $^1$H NMR spectrum of the diastereomeric camphorsulfonamides, the resonances due to the terminal methyl group of the diamine moiety are fully resolved, even at low field strength. Conversion of resolved diamines (R)-2 and (S)-2 to the enantiomers of hydroxychloroquine, (R)-1a and (S)-1a, involves heating (R)-2 and (S)-2 with 4,7-dichloroquinoline in the presence of diisopropylethylamine. Optimum conditions are different for the two enantiomers: at 135° C., (S)-2 is consistently more prone to degradation than (R)-2, and the conversion is correspondingly less clean. Larger scale purification of (R)-1a and (S)-1a is performed by acid-base extraction. Below pH 5, excess dichloroquinoline is removed from the aqueous phase, and the remaining impurities is removed by further extraction between pH 7 and pH 8, followed by charcoal treatment of the aqueous phase to remove a trace of highly-coloured material. Above pH 8 (the most convenient pH being around 12), pure hydroxychloroquine is extracted. Both (R)-1a and (S)-1a are oils, and require protection from light during storage, developing a yellow color otherwise. After purification, enantiomers (R)-1a and (S)-1a are converted to bis(dihydrogenphosphate) salts, ((R)-b and ((S)-1b), by treatment with phosphoric acid (two molar equivalents). Where triethylamine remained from the preceding chromatographic step, this is removed by trituration with acetone to leave a deliquescent hydrate. Phosphoric acid (19.7 ml, 0.29 mol) was added to (S)-1a (43.4 g, 0.144 mol) with ice cooling to moderate the reaction. The resulting gum was ground under acetone and the resulting deliquescent solid was filtered quickly, suspended immediately in fresh acetone (200 ml), then stirred overnight. Dehydration by heating in ethanolic suspension gives friable white solids. Rapid filtration gave a white powder which was transferred immediately into a flask containing ethanol (200 ml). The resulting suspension was refluxed for four days, then filtered, and the solid washed with ethanol. After drying under vacuum to constant weight, the yield of (S)-1b was 52.6 g (69%). (R)-1a is converted to bis(dihydrogenphosphate) salt in an analogous manner. Both anhydrous samples and monohydrates melt at 192° C., substantially higher than the melting point of 168-170° C. reported for the racemate. The enantiomers give substantial and reproducible rotations, and as little as 0.5% of the minor enantiomer can be detected by HPLC using a chiral AGP stationary phase. Thus, both polarimetry and HPLC are suitable for determination of the optical purity of the enantiomers. Hydroxychloroquine sulfate is also commercially available, and can be purchased from 3B Scientific Corporation™, (catalog No., DR001622).

Methods of Use

Methods for treatment of inflammatory conditions, steatohepatitis and inflammation associated liver cancer are also encompassed by the present invention. Said methods of the invention include administering a therapeutically effective amount of clemizole and/or R-chloroquine to a subject in need thereof.

The present invention also provides methods for the treatment of an inflammatory condition, comprising administering to a subject one or more compounds or a composition comprising one or more compounds of the invention and a pharmaceutically acceptable vehicle. The present invention also provides methods for the treatment or prevention of inflammatory conditions in combination with anti-inflammatory treatments presently utilized in the clinic. Examples of anti-inflammatory treatments include, but are not limited to, non-steroidal anti-inflammatory drugs such as, aspirin, ibuprofen and naproxen, corticosteroids, anti-inflammatory bioactive compounds such as, plumbagin or immune selective anti-inflammatory derivatives.

The present invention provides methods for the treatment of non-alcoholic steatohepatitis comprising administering to a subject one or more compounds or a composition comprising one or more compounds of the invention and a pharmaceutically acceptable vehicle. As used herein, the term "non-alcoholic steatohepatitis" refers to liver diseases characterized by inflammation of the liver with concurrent fat accumulation in the liver. The invention also provides methods for the treatment of non-alcoholic steatohepatitis in combination with treatments presently utilized in the clinic for the treatment of conditions commonly associated with non-alcoholic steatohepatitis, such as metabolic syndrome and/or diabetes mellitus. Non-limiting examples of treatments for metabolic syndrome and/or diabetes mellitus include, treatments to reduce insulin resistance, cholesterol and triglycerides. Examples of treatments that reduce insulin resistance, include but are not limited to, metformin, thiazolidinedione, pioglitazone and rosiglitazone. Examples of treatments for hypercholesterolemia include, but are not limited to, statin, bile acid sequestrants, cholesterol absorption inhibitors, a fibric acid derivatives or nicotinic acid.

The present invention provides methods for the treatment or prevention of liver cancer, comprising administering to a subject one or more compounds or a composition comprising one or more compounds of the invention and a pharmaceutically acceptable vehicle. As used herein, the term "liver cancer" refers to hyperproliferative diseases of the liver, including, but not limited to, hepatocellular carcinoma, fibrolamellar hepatocellular carcinoma, cholangiocarcinoma, angiosarcoma, secondary or metastatic liver cancer and hepatoblastoma. The present invention also provides methods for the treatment or prevention of liver cancer in combination with treatments presently utilized in the clinic for the treatment or prevention of liver cancer, including, but not limited to, chemotherapeutic agents.

Pharmaceutical Compositions of the Invention

The clemizole and R-chloroquine of the invention can be formulated in pharmaceutical compositions. These compositions can comprise, in addition to clemizole and/or R-chloroquine, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

The small molecule useful compound according to the present invention that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of the condition being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pennsylvania: Mack Publishing Company, 1990); Carey and Sundberg Advanced Organic Chemistry 3rd Ed. (Plenum Press) Vols A and B (1992).

Pharmaceutical Compositions and Route of Drug Administration

Compounds A, B, C, D and Vehicle were orally administered in a volume of 5 mL/kg. Compound A comprised a recemic mixture of R-chloroquine and S-chloroquine.

Compound B comprised R-chloroquine. Compound C comprised S-chloroquine.

Compound D comprised clemizole. All test compounds were weighed and dissolved in vehicle (5% DMSO/Water).

Treatment Doses of Drug

Compounds A, B, and C were orally administered at doses of 258 mg/kg on the first 2 days and 129 mg/kg thereafter once daily. Compound D was orally administered at doses of 89 mg/kg twice daily. Table 1 below summarizes the treatment schedule.

TABLE 1

Treatment schedule for study groups

| Group | No. mice | Mice | Test substance | Dose (mg/kg) | Volume (mL/kg) | Regimens | Sacrifice (9 wk) | Sacrifice (18 wk) |
|---|---|---|---|---|---|---|---|---|
| 1 | 11 | STAM | Vehicle | — | 5 | Oral, once daily, 6 wks-18 wks | 6 | 4 |
| 2 | 11 | STAM | Compound A (R-chloroquine and S-chloroquine) | 258* 129 | 5 | Oral, once daily, 6 wks-18 wks | 6 | 4 |
| 3 | 11 | STAM | Compound B (R-chloroquine) | 258* 129 | 5 | Oral, once daily, 6 wks-18 wks | 6 | 4 |
| 4 | 11 | STAM | Compound C (S-chloroquine) | 258* 129 | 5 | Oral, once daily, 6 wks-18 wks | 6 | 4 |
| 5 | 11 | STAM | Compound D (clemizole) | 89 | 5 | Oral, twice daily, 6 wks-18 wks | 6 | 4 |

*258 mg/kg: Only first 2 days.

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

Methods

Induction of Non-Alcoholic Steatohepatitis

NASH was induced in 55 male mice by a single subcutaneous injection of 200 μg streptozotocin (STZ, Sigma-Aldrich, USA) solution 2 days after birth and feeding with high fat diet (HFD, 57 kcal % fat, cat #: HFD32, CLEA Japan, Inc., Japan) after 4 weeks of age. Mice that had been induced have NASH by this method are referred to below as NASH mice.

Animals

C57BL/6 mice (14-day-pregnant female) were obtained from Japan SLC, Inc. (Shizuoka, Japan). All animals used in the study were housed and cared for in accordance with the Japanese Pharmacological Society Guidelines for Animal Use.

Plasma Sampling and Measurement of Whole Blood and Plasma Biochemistry

Non-fasting blood was collected in polypropylene tubes with anticoagulant (Novo-heparin, Mochida Pharmaceutical, Japan) from submandibular bleeding at 6 (before dosing), 7 and 8 weeks of age. The collected blood samples were centrifuged and the supernatant were collected as heparinized plasma.

Non-fasting blood glucose in whole blood was measured using LIFE CHECK (EIDIA Co. Ltd., Japan). Plasma ALT was measured by FUJI DRI-CHEM 7000 (Fujifilm Corporation, Japan).

Histopathological Analyses

For HE staining, sections were cut from paraffin blocks of liver tissue prefixed in Bouin's solution and stained with Lillie-Mayer's Hematoxylin (Muto Pure Chemicals Co., Ltd., Japan) and eosin solution (Wako Pure Chemical Industries). NAFLD Activity score (NAS) was calculated according to the criteria of Kleiner (Kleiner D E. et al., Hepatology, 2005; 41:1313). To visualize collagen deposition, Bouin's fixed liver sections were stained using picro-Sirius red solution (Waldeck, Germany).

For quantitative analysis of fibrosis areas bright field images of Sirius red-stained sections were captured around the central vein for livers using a digital camera (DFC280; Leica, Germany) at 200-fold magnification, and the positive areas in 5 fields/section were measured using ImageJ software (National Institute of Health, USA).

Macroscopic Analyses of Livers

The number of macroscopically visible tumor nodules formed on the liver surface was measured. The maximum diameter of macroscopically visible tumor nodules formed on the liver surface was measured.

Statistical Tests

Statistical analyses were performed using Bonferroni Multiple Comparison Test on GraphPad Prism 4 (GraphPad Software Inc., USA). P values<0.05 were considered statistically significant.

Example 1: Administration of S-Chloroquine Results in Reduced Liver and Body Weight in Mice with NASH Body weight in the all groups did not obviously change during the treatment period (Table 2). There were no significant differences in mean body weight between the Vehicle group and all Compound groups. During the treatment period, mice died before reaching week 9 as follows; one out of 11 mice died in all groups.

The Compound C group significantly decreased the mean body weight on the day of sacrifice (Table 2). There were no significant differences in the mean body weight on the day of sacrifice between the Vehicle group and the Compound A, Compound B and Compound D groups.

The Compound C group significantly decreased the mean liver weight (Table 2). There were no significant differences in the mean liver weight on the day of sacrifice between the Vehicle group and the Compound A, Compound B and Compound D groups. There were no significant differences in the mean liver-to-body weight ratio on the day of sacrifice between the Vehicle group and the Compound A, Compound B, Compound C and Compound D groups.

TABLE 2

Body weight and liver weight in NASH mice

| Parameter (mean ± SD) | Vehicle (n = 6) | Compound A (n = 6) | Compound B (n = 6) | Compound C (n = 6) | Compound D (n = 6) |
| --- | --- | --- | --- | --- | --- |
| Body weight (g) | 16.9 ± 2.1 | 15.0 ± 1.9 | 14.5 ± 2.4 | 13.7 ± 1.3 | 15.5 ± 1.5 |
| Liver weight (mg) | 1082 ± 130 | 1045 ± 243 | 934 ± 135 | 810 ± 77 | 1047 ± 76 |
| Liver-to-body weight ratio (%) | 6.5 ± 0.9 | 7.0 ± 1.4 | 6.5 ± 0.4 | 5.9 ± 0.4 | 6.8 ± 0.4 |

Example 2: Whole Blood Biochemistry in Mice Administered with Chloroquine or Clemizole in NASH Mice There were no significant differences in the whole blood glucose levels during the study period between the Vehicle group and the Compound A, Compound B, Compound C and Compound D groups. Plasma ALT levels were measured at the time of sacrifice between the Vehicle group and the Compound A, Compound B, Compound C and Compound D groups (Table 3).

TABLE 3

ALT levels of NASH mice treated with test compounds.

| Parameter (mean ± SD) | Vehicle (n = 6) | Compound A (n = 6) | Compound B (n = 6) | Compound C (n = 6) | Compound D (n = 6) |
| --- | --- | --- | --- | --- | --- |
| Plasma ALT (U/L) | 22 ± 11 | 21 ± 13 | 14 ± 6 | 9 ± 3 | 18 ± 10 |

Example 3: Reduced NAFLD Activity Score is Observed in NASH Mice Treated with R-Chloroquine or Clemizole Hematoxylin and Eosin staining was performed on liver tissue sections from mice treated with test compounds and NAFLD Activity scores were calculated (Table 4). The Compound B and Compound D groups showed significant reduction in NAS compared with the Vehicle group.

TABLE 4

NAFLD activity scores of NASH mice treated with test compounds.

| Group | n | Steatosis | | | | Lobular inflammation | | | | Hepatocyte ballooning | | | NAS (mean ± SD) |
|---|---|---|---|---|---|---|---|---|---|---|---|---|---|
| | | 0 | 1 | 2 | 3 | 0 | 1 | 2 | 3 | 0 | 1 | 2 | |
| Vehicle | 6 | — | 4 | 2 | — | — | — | 4 | 2 | — | — | 6 | 5.7 ± 0.8 |
| Compound A | 6 | 1 | 5 | — | — | — | — | 1 | 5 | — | 3 | 3 | 5.2 ± 0.8 |
| Compound B | 6 | 1 | 5 | — | — | — | 2 | 4 | — | — | 1 | 5 | 4.3 ± 0.5 |
| Compound C | 6 | — | 6 | — | — | — | — | 4 | 2 | — | — | 6 | 5.3 ± 0.5 |
| Compound D | 6 | 1 | 5 | — | — | — | 4 | 1 | 1 | — | — | 6 | 4.3 ± 1.0 |

Definition of NAS Components

| Item | Score | Extent |
|---|---|---|
| Stetosis | 0 | <5% |
| | 1 | 5-33% |
| | 2 | >33-66% |
| | 3 | >66% |
| Hepatocyte Ballooning | 0 | None |
| | 1 | Few Balloon cells |
| | 2 | Many cells/prominent ballooning |
| Lobula Inflammation | 0 | No foci |
| | 1 | <2 foci/200x |
| | 2 | 2-4 foci/200x |
| | 3 | >4 foci/200x |

Example 4: Liver Fibrosis Area is not Affected by Administration of Test Compounds in NASH Mice Liver sirius red staining was performed on liver sections of NASH mice treated with test compounds (Table 5). There were no significant differences in the fibrosis area at the time of sacrifice between the Vehicle group and the Compound A, Compound B, Compound C and Compound D groups.

TABLE 5

Fibrosis Area of livers of NASH mice administered with TEST compounds.

| Parameter (mean ± SD) | Vehicle (n = 6) | Compound A (n = 6) | Compound B (n = 6) | Compound C (n = 6) | Compound D (n = 6) |
|---|---|---|---|---|---|
| Sirius red-positive area (%) | 1.13 ± 0.17 | 0.87 ± 0.23 | 0.78 ± 0.35 | 0.90 ± 0.44 | 0.95 ± 0.39 |

Example 5: Body Weight and Liver Weight of Mice with NASH-Induced Hepatocellular Carcinoma Administered with Test Compounds Body weight in the all study groups did not obviously change during the treatment period (Table 6). There were no significant differences in mean body weight between the Vehicle group and all Compound groups (Table 6). During the treatment period, mice died before reaching week 18 as follows; one out of 4 mice died in the Vehicle and the Compound D groups. Two out of 4 mice died in the Compound B and the Compound C groups. Three out of 4 mice died in the Compound A group. The mean(s)±SD were shown in Table 6.

TABLE 6

Organ and liver-to-body weight ratio of NASH
induced HCC mice treated with test compounds

| Parameter<br>(mean ± SD) | Vehicle<br>(n = 3) | Compound A<br>(n = 1) | Compound B<br>(n = 2) | Compound C<br>(n = 2) | Compormd D<br>(n = 3) |
|---|---|---|---|---|---|
| Body weight (g) | 24.6 ± 2.1 | 17.5 ± 0.0 | 20.4 ± 0.3 | 17.9 ± 2.8 | 18.8 ± 3.8 |
| Liver weight (mg) | 2059 ± 667 | 1443 ± 0 | 1616 ± 635 | 1353 ± 178 | 1710 ± 113 |
| Liver-to-body<br>weight ratio (%) | 8.3 ± 2.5 | 8.2 ± 0.0 | 7.9 ± 3.0 | 7.6 ± 0.1 | 6.3 ± 0.8 |

Figure 8:
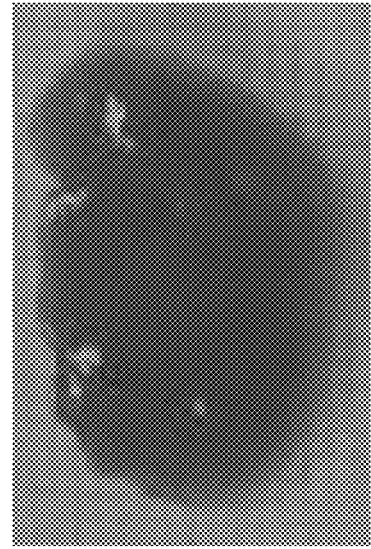
FIG. 8: Representative images of mouse livers depicting inhibition of tumor formation in mice treated with clemizole (compound D) are shown.
Figure 8:
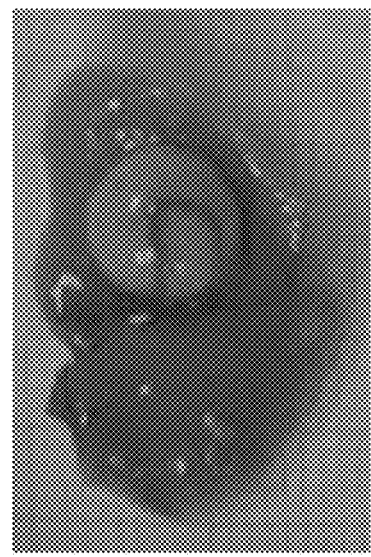

Example 6: Administration of Clemizole in Mice with Hepatocellular Carcinoma Reduces Liver Tumor Diameter and Number of Tumor Nodules The number of macroscopically visible tumor nodules formed on the liver surface was measured. The maximum diameter of macroscopically visible tumor nodules formed on the liver surface was measured (Table 7). All surviving mice (n=3) showed visible tumor nodules on the liver surface in the Vehicle group. Absence of visible tumor nodules on the liver surface was observed in 2 out of 3 survived mice in the Compound D (clemizole) group (FIG. 8). The mean(s)±SD are shown in Table 7.

TABLE 7

Maximum diameter of visible tumor nodules in
mice with HCC treated with test compounds.

| Parameter<br>(mean ± SD) | Vehicle<br>(n = 3) | Compound A<br>(n = 1) | Compound B<br>(n = 2) | Compound C<br>(n = 2) | Compound D<br>(n = 3) |
|---|---|---|---|---|---|
| Number of nodules | 3.0 ± 2.0 | 2.0 ± 0.0 | 2.0 ± 1.4 | 1.5 ± 2.1 | 0.3 ± 0.6 |
| Maximum diameter of nodules (mm) | 7.3 ± 6.5 | 6.1 ± 0.0 | 11.1 ± 7.0 | 3.5 ± 5.0 | 0.7 ± 1.2 |

Example 7: Human Patients with Hepatocellular Carcinoma (HCC) Treated with Clemizole A phase IIa, open label pilot study is conducted to test the safety, tolerability, pharmacokinetic and pharmacodynamic activity of 200 mg vs. 400 mg vs. 500 mg clemizole hydrochloride given orally thrice daily, to subjects with hepatocellular carcinoma (HCC) that are either awaiting liver transplantation or have an unresectable lesion. The completed study treats up to 40 patients. Initial clinical results from two patients with hepatocellular carcinoma who were administered 200 mg clemizole for 3 or 5 months are described below.

Patient #1 Summary:

Patient #1 is a 70 year old man, diagnosed with HCC in the setting of chronic hepatitis B-induced cirrhosis. Diagnosis was determined by dynamic liver CT. Patient #1 had received radiofrequencey ablation treatment for HCC in 2011, but experienced progression of disease post-treatment. Patient #1 also received three courses of transarterial chemoembolization (TACE) in April-May 2015 and June 2015. Patient #1 presented stable disease for a period of about 5 months prior to progression of HCC. The patient then began clemizole treatment with oral administration of 200 mg clemizole thrice daily. After 3 months of clemizole treatment, the patient underwent follow up dynamic liver CT imaging, and when a significant increase in tumor size would have been expected in the absence of any therapy, the HCC remained stable. At that time, the patient felt well with no complaints or side effects.

Patient #2 Summary:

Patient #2 is a 77 year old man, diagnosed with multifocal HCC in the setting of chronic hepatitis B-induced cirrhosis. Diagnosis was determined by dynamic liver magnetic resonance imaging. Patient #2 had failed and/or not tolerated sorafenib treatment and presented with disease progression post-treatment. Patient #2 then initiated clemizole treatment with oral administration of 200 mg clemizole thrice daily. After 5 months of clemizole treatment, the patient underwent follow up dynamic liver magnetic resonance imaging, and when a significant increase in tumor size would have been expected in the absence of any therapy, the HCC remained stable. At that time, the patient felt very well with no complaints or side effects.

Although a small number of patients have been treated to date, the observed efficacy and tolerability with the low dose clemizole used (i.e. 200 mg vs. up to 500 mg in subsequent patients) are very exciting in their own right, especially when compared to the only approved therapy for HCC, sorafenib. In the sorafenib phase 2 study (Abou-Alpha et al. Journal Clinical Oncology 2006, 24(26): 4293-4300), the median time to progression (TTP) was 4.2 months. Toxicities included diarrhea in over 40%, hand-foot skin reaction in over 30%, and fatigue in 30%, including grade 3/4 drug-related toxicities such as fatigue (9.5%), diarrhea (8.0%), and hand-foot skin reaction (5.1%). In the sorafenib phase 3 study (Llovet et al. NEJM 2008; 359:378-90), the median time to radiologic progression was 5.5 months in the sorafenib group and 2.8 months in the placebo group. The overall incidence of treatment-related adverse events was 80% in the sorafenib group. These were predominantly gastrointestinal, constitutional, or dermatologic in nature (grade 1 or 2 in severity), as well as hypophosphatemia (11% grade 3) and thrombocytopenia (4% grade 3 or 4).

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A method for treating lobular inflammation in a subject who has non-alcoholic fatty liver disease (NAFLD) or non-alcoholic steatohepatitis (NASH), comprising:
   administering to the subject an effective amount of clemizole, a deuterated analog of clemizole, or a clemizole metabolite.

2. The method of claim 1, wherein the effective amount is 200-500 mg administered daily, twice daily, or thrice daily.

3. The method of claim 1, wherein the clemizole, the deuterated analog of clemizole, or the clemizole metabolite is administered for greater than 2 months.

4. The method of claim 1, wherein a result of the administering is reduction of inflammation, improved organ function, or reduced risk of development of disease or disease progression.

5. The method of claim 1, wherein the administration is oral.

6. The method of claim 1, wherein the administrating is intravenous.

7. The method of claim 1, further comprising administering an effective amount of an inhibitor of CYP3A4.

8. The method of claim 7, wherein the inhibitor of CYP3A4 is ritonavir or cobicistat.

9. The method of claim 1, further comprising administering a second anti-inflammatory treatment.

10. The method of claim 9, wherein the second anti-inflammatory treatment comprises: aspirin, ibuprofen, naproxen, corticosteroids, plumbagin, or immune selective anti-inflammatory derivatives.

11. The method of claim 1, wherein the subject is administered the clemizole.

12. The method of claim 1, wherein the lobular inflammation occurs in a subject with non-alcoholic steatohepatitis (NASH).

13. The method of claim 1, wherein the lobular inflammation is characterized by an elevated plasma level of alanine aminotransferase in the plasma of the subject as compared to a level associated with a normal healthy control population.

14. The method of claim 1, wherein the lobular inflammation in the subject is lobular inflammation characterized by a plurality of foci of infiltrating immune cells in a histological sample.

15. The method of claim 1, wherein the lobular inflammation in the subject is diagnosed from examination of a sample obtained from a liver biopsy.

16. The method of claim 1, wherein the lobular inflammation in the subject is diagnosed by ultrasound, computerized tomography, magnetic resonance imaging, a blood test, or NMR spectroscopy, including hyperpolarized $^{13}$C-NMR spectroscopy.

17. The method of claim 1, wherein the administering significantly reduces the subject's plasma level of alanine aminotransferase.

18. The method of claim 1, further comprising administering an effective amount of an anti-NASH agent.

19. The method of claim 18, wherein the anti-NASH agent is an FXR agonist, an LOXL2 inhibitor, a caspase protease inhibitor, cysteamine bitartrate, a galectin-3 inhibitor, a CCR2 and CCR5 pathway inhibitor, a cysteine depleting agent, a SGLT-2 inhibitor, GLP-1, bile acids, synthetic fatty acid and bile acid conjugates, a Sirtuin stimulant, an immunomodulator, or a PPAR agonist.

20. The method of claim 1, further comprising treating the subject for insulin resistance by administering to the subject an effective amount of a medicament that increases insulin sensitivity in the subject.

21. The method of claim 20, wherein the medicament that increases insulin sensitivity is metformin, thiazolidinedione, pioglitazone, or rosiglitazone.

22. The method of claim 1, further comprising administering to the subject an effective amount of a medicament that decreases cholesterol and/or high triglycerides in the subject.

23. The method of claim 22, wherein the medicament that decreases cholesterol and/or high triglycerides is a statin, a bile acid sequestrant, a cholesterol absorption inhibitor, a fibric acid derivative, or nicotinic acid.

24. The method of claim 12, further comprising administering an effective amount of an inhibitor of CYP3A4.

25. The method of claim 24, wherein the inhibitor of CYP3A4 is ritonavir or cobicistat.

* * * * *

UNITED STATES PATENT AND TRADEMARK OFFICE
CERTIFICATE OF CORRECTION

Page 1 of 1

PATENT NO. : 12,090,141 B2
APPLICATION NO. : 16/869312
DATED : September 17, 2024
INVENTOR(S) : Glenn et al.

It is certified that error appears in the above-identified patent and that said Letters Patent is hereby corrected as shown below:

In the Claims

In Column 21, in Claim 5, Line 22, delete "administration" and insert -- administering --, therefor.

In Column 21, in Claim 6, Line 24, delete "administrating" and insert -- administering --, therefor.

Signed and Sealed this
Twenty-sixth Day of November, 2024

Katherine Kelly Vidal
*Director of the United States Patent and Trademark Office*